United States Patent [19]

Conner et al.

[11] 4,038,294

[45] July 26, 1977

[54] FATTY HALO ALKANOATE QUATERNARIES OF DIALKYLAMINOPROPYLAMIDES

[75] Inventors: Donald E. Conner, Clifton; Arnold W. Fogel, Park Ridge, both of N.J.

[73] Assignee: Van Dyk & Company, Incorporated, Belleville, N.J.

[21] Appl. No.: 676,416

[22] Filed: Apr. 13, 1976

[51] Int. Cl.$^2$ .......................... C09F 5/00; C11C 3/00
[52] U.S. Cl. .............. 260/404.5; 260/482 R; 424/70; 424/320; 424/329
[58] Field of Search ............ 260/404.5, 482 R; 424/70, 320, 329

[56] References Cited

U.S. PATENT DOCUMENTS

| | | | |
|---|---|---|---|
| 2,686,795 | 8/1954 | Koebner | 260/404.5 |
| 2,710,876 | 6/1955 | Krebs et al. | 260/482 R |
| 2,777,872 | 1/1957 | Shacklett | 260/482 R |
| 3,225,074 | 12/1965 | Cowen et al. | 260/404.5 |
| 3,492,324 | 1/1970 | Blackman | 260/404.5 |
| 3,751,451 | 8/1973 | Samour et al. | 260/482 R |
| 3,855,290 | 12/1974 | Zak et al. | 424/329 |
| 3,959,461 | 5/1976 | Bailey et al. | 260/404.5 |

*Primary Examiner*—Winston A. Douglas
*Assistant Examiner*—John F. Niebling

[57] ABSTRACT

Novel compositions of matter consisting of fatty halo alkanoate quaternaries of dialkylaminopropylamides have been found to be excellent emollients having surprisingly good anti-tangle and anti-static properties in hair preparations. They are prepared by reacting the dialkylaminopropylamides with fatty halo alkanoate esters.

6 Claims, No Drawings

FATTY HALO ALKANOATE QUATERNARIES OF DIALKYLAMINOPROPYLAMIDES

FIELD OF THE INVENTION

There is an ever-increasing need for improved emollients, particularly those having superior hair conditioning properties in view of the increased emphasis on hair styling for fashion purposes. This invention provides novel synthetic emollients having outstanding properties for the purposes mentioned.

Many emollients employed in hair conditioning either left the hair over fatted or static prone. They also presented formulation problems.

As part of the continuing attempt to prepare quaternary halides of various amides which could overcome these problems, e.g. gluconamide, it was found that reaction with higher alkyl chlorides, e.g. 2-ethyl, hexyl or decyl resulted in the decomposition of the gluconamide at the temperatures (120°-140° C.) necessary to bring about quaternary formation. This severely limited the synthetic possibilities.

SUMMARY OF THE INVENTION

It has now been found that fatty halo alkanoate quarternaries of dialkyl amino propyl amides, corresponding to the following formula:

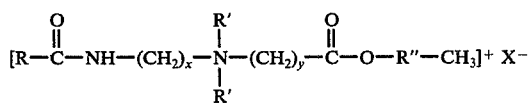

wherein the RCO moiety is selected from the group consisting of gluconic acid, and $C_7$-$C_{21}$ fatty acids; $R'$ is an alkyl group having from 1 to 2 carbon atoms; $x$ is an integer of from 2 to 3; $y$ is an integer of from 1 to 3; $R''$ is selected from the group consisting of $(CH_2)_{(7-21)}$ and sorbate; and X is halogen, are extremely effective emollients imparting excellent anti-tangle and anti-static properties, the latter even after dry combing. This is indeed surprising considering properties of the prior art materials. The compositions of this invention furthermore are relatively non-irritating and easy to formulate requiring no salt or acid.

DISCUSSION OF PREFERRED EMBODIMENTS

The novel products of this invention can be prepared as follows: The corresponding oil, or acid, is reacted, e.g. with either gamma dimethylamino or gamma diethylaminopropylamine, at between about 140°-160° C. using an alkaline catalyst and a nitrogen atmosphere which inhibits oxidation of unsaturated fatty acids. It has been found that an alkaline catalyst such as sodium hydroxide, potassium hydroxide and sodium methylate or ethylate work equally well.

The amide is then quaternized by reaction with the fatty halo alkanoate ester at temperatures in the range of about 100° to 110° C., utilizing glycols, e.g. propylene glycol, as a solvent.

Sources of the R are exemplified by gluconic acid, mink oil fatty acids, safflower fatty acids, hydrogenated tallow triglycerides, corn oil fatty acids, stearic, palmitic, myristic and lauric acids. The sources can be saturated or unsaturated, in the latter case can have up to 3 double bonds conjugated or unconjugated.

Especially preferred halides are chlorides and bromides.

Examples of chloro esters utilized are myristyl; cetyl; and sorbitol chloro acetates; and decyl propionate.

Thus, particularly effective compositions are those in which the RCO is the moiety from gluconic acid, safflower fatty acids, and hydrogenated tallow triglycerides; $R'$ is $CH_3$; $x$ is 3; $y$ is 1; $R''$ is $(CH_2)_{13}$; and X is Cl.

This invention, product workup and properties of these novel materials will be better understood by reference to the following examples.

EXAMPLE 1

MYRISTYL 3-CHLOROPROPIONATE OF 3-DIMETHYLAMINOPROPYL MINK OIL FATTY ACID AMIDE 170-3g Mink 3-dimethylaminopropylamide
152g Myristyl 3-chloropropionate
215g propylene glycol After heating the above materials for 4 hours at 110° C., the theoretical chloride (2.9%) was obtained.

| Analyses: | % Ionic Chloride = 2.9% |
|---|---|
| | % Solids = 60% |
| | % Propylene glycol = 40% |

EXAMPLE 2

SORBITOL CHLORO ACETATE QUATERNARY OF 3-DIMETHYLAMINOPROPYLAMIDE OF MINK OIL FATTY ACIDS

193g Mink oil amide
137g Sorbitol cloro acetate
220g propylene glycol

The above materials were heated at 110° C. for 2 hours in order to obtain the theoretical 3.2% ionic chloride. Product is a light amber viscous liquid at room temperture.

| Analyses: | % Ionic Chloride = 3.2% |
|---|---|
| | % Solids = 60% |
| | % Propylene glycol = 40% |

EXAMPLE 3

TETRADECYL CHLORO ACETATE QUATERNARY OF MINK OIL 3-DIMETHYLAMINOPROPYLAMIDE

Part A: [Amide formation]

Mink oil, a mixture of triglyceride containing myristic, palmitic, palmitoleic, stearic, oleic and linoleic acids, is reacted with 3-dimethylaminopropylamide using potassium hydroxide as the transamidation catalyst.

164g Mink oil
74g Diethylaminopropylamine
2g KOH

The above materials were heated, with agitation in a flask, at 140°-150° C. for 6 hrs. under a nitrogen atmosphere. An alkali number of 152 was obtained. Part B1: [Quaternary formation]

After cooling the above material to 50° C., 201g of water and 201g propylene glycol were added. The mixture was agitated until homogeneous, then 162g of myristyl chloro acetate was added. The required ionic chloride of 2.5 was obtained after refluxing at 105° C. for 10-12 hrs.

| Analyses: | % Ionic chloride = 2.5% |
|---|---|
| | % Solids = 50% |
| | % Water = 25% |
| | % Propylene glycol = 25% |

Part B2: [Quaternary formation]
192.5g Mink amide
159.5g Myristyl chloro acetate
234.5g Propylene glycol The theoretical chloride of 3% was obtained by heating the above materials at 110° C. for 2 ½ hrs.

| Analyses: | % Ionic chloride = 3% |
|---|---|
| | % Solids = 60% |
| | % Propylene glycol = 40% |

This material has the advantage over the product described in B1 in that it is a liquid with the viscosity of glycerol at room temperature, the other material is a gel when cooled to room temperature.

EXAMPLE 4

TETRADECYL CHLORO ACETATE QUATERNARY OF 3-DIMETHYLAMINOPROPYL GLUCONAMIDE

Part A: [3-diemthylaminopropyl gluconamide]
178g Glucono delta lactone
102g Dimethylaminopropylamine
571g Isopropanol An acid value of 0.3 was obtained after refluxing the above materials at 87° C. for 1 hr.

Part B: [Quaternary formation]

After cooling the above solution to 50%, 291 g of myristyl chloro acetate was added. The ionic chloride reached a maximum value of 2.9% [3.1% is theoretical] after refluxing at 86° C. for 5 hrs. Upon cooling to room temperature, the solution solidified into a soft solid.

| Analyses: | % Ionic chloride = 2.9% |
|---|---|
| | % Solids = 50% |
| | % Isopropanol = 50% |
| | 2% Solution in ethanol - insoluble |
| | 2% Solution in water - dispersible |

EXAMPLE 5

DODECYL CHLORO ACETATE QUATERNARY OF 3-DIMETHYLAMINOPROPYL GLUCONAMIDE

Part A: [3-dimethylaminopropyl gluconamide]
178g Glucono delta lactone
102g Dimethylaminopropylamine
543g Isopropanol After heating the above mixture under reflux at 87° C. for 1 hr. an acid value 0.2 was obtained. The mixture was cooled to 50° C.

Part B: [Quaternary formation]

To the above solution 263g lauryl chloro acetate was added. An ionic chloride of 3.3% [theoretical] was obtained after a 5 hr. reflux. Product solution cooled to 50° C. and transferred to a jar, where, upon cooling to room temperature, it became a soft solid.

| Analyses: | % Ionic chloride = 3.3% |
|---|---|
| | % Solids = 50% |
| | % Isopropanol = 50% |
| | 2% Solution in ethanol = insoluble |
| | 2% Solution in water = dispersible |

EXAMPLE 6

DECYL CHLORO ACETATE QUATERNARY OF 3-DIMETHYLAMINOPROPYL GLUCONAMIDE

Part A: [3-diemthylaminopropyl gluconamide]
178g Glucono delta lactone
102g Dimethylaminopropylamine
515g Isopropanol The above materials were heated under reflux in a 2 liter flask equipped with a thermometer, stirrer and reflux condenser, for 1 hour. An acid value of 0.2 indicates complete reaction.

Part B: [Quaternary formation]

After cooling to about 60° C., 235 g of decylchloro acetate was added. An ionic chloride of 3.4% [3.4% is theoretical] was obtained after a 5 hour reflux at 86° C. After cooling to 50° C., the liquid was poured into a jar, where upon cooling to room temperature, the material became a soft solid.

| Analyses: | Ionic chloride = 3.4% |
|---|---|
| | % Solids = 50% |
| | % Isopropanol = 50% |
| | 2% Solution in ethanol - insoluble |
| | 2% Solution in water - dispersible |

EXAMPLE 7

SORBITOL MONOCHLORO ACETATE

| Charge: | 520g Sorbitol (70% solution) |
|---|---|
| | 189g Chloro acetic acid |
| | 150g Toluene |

The above materials were heated under reflux in a 2 liter flask fitted with a thermometer, stirrer and water trap. Most of the water [188g] was removed at or below 90° C. An acid value of 18.4 was obtained at this point. Heating at 110° C. for an additional hour yielded an additional 18g of water; the acid value was reduced to 3.8% where it remained.

Upon cooling a clear very viscous liquid was obtained.

| Analyses: | Acid value = 3.8% |
|---|---|
| | Saponification value = 453.5 |
| | % Chloride = 13.9% |

EXAMPLE 8

OCTADECYL MONOCHLORO ACETATE

| Charge: | 540g Octadecyl alcohol (stearyl) |
|---|---|
| | 199g Chloro acetic acid |
| | 200 ml toluene |
| | 36g water to be removed |

The above material was refluxed in a 2 liter flask equipped with a thermometer, stirrer, water separator, to a maximum temperature of 139° C. After 1½ hrs. all the water [36g] was removed.

After neutralizing with 5% sodium carbonate and water, toluene was removed under water jet vacuum in a pot temperature of 129° C. High vacuum distillation of the crude gave the following results:

| Fr. No. 1 | 198–201° C./3 min. | 58g |
| Fr. No. 2 | 124° C./3 min. | 400g |
| Fr. No. 3 | 125° C./3 min. | 194g |

Analyses of Fractions:

| Analyses of Fractions: | |
|---|---|
| 1st fraction | Acid value = 1.8 |
| | Saponificaton = 307.6 |
| | % Chloride = 9.7% |
| | % Ester = 94.5% |
| | % alcohol = 5.5% |
| 2nd fraction | Acid value = 0.7 |
| | Saponification value = 321.2 |
| | % Chloride = 10.1% |
| | % Ester = 99% |
| | % Alcohol = 1% |
| 3rd fraction | Acid value = 0.5 |
| | Saponification value = 320.4 |
| | % Chloride = 10.0 |
| | % Ester = 98.8% |
| | % Alcohol = 1.2% |

Total weight of ester = 642.4g
Yield of ester - 92.7% of theory

EXAMPLE 9

TETRADECYL MONOCHLORO ACETATE

| Charge: | 190g Chloro acetic acid |
|---|---|
| | 428g Tetradecyl alcohol (myristyl) |
| | 250 ml toluene |
| | 1g para toluene sulfonic acid |
| | 36g of water to be removed |

After refluxing the above materials in a 2 liter flask, equipped with a thermometer, stirrer, and water separator, for 1½ hrs. The required amount of water was collected. The maxiumum temperature reached during this reflux period was 141° C.

The ester solution was neutralized with 5% sodium carbonate and washed free of excess alkali with water.

Toluene was removed under water jet vacuum [max. temp. 140° C.] and the crude distilled under high vacuum.

| Fr. No. 1 | 150–160° C./1 min. | 106g |
| Fr. No. 2 | 160–169° C./1 min. | 450g |

Analyses of Fractions:

| Analyses of Fractions: | |
|---|---|
| 1st fraction | Acid value = 0.50 |
| | Saponification value = 160.2 |
| | % Chloride = 10.1% |
| | % Ester = 83% |
| | % Alcohol = 17% |
| 2nd fraction | Acid value = 0.13 |
| | Saponification value = 181 |
| | % Chloride = 11.5% |
| | % Ester = 94% |
| | % Alcohol = 6% |

Total ester content = 511g
Yield of ester = 88% of theory

EXAMPLE 10

DODECYL MONOCHLORO ACETATE

| Charge: | 372g Dodecyl alcohol (lauryl) |
|---|---|
| | 209g Chloro acetic acid |
| | 250 ml toluene |
| | 36g water to be removed |

The required amount of water (36g) was removed after refluxing the above materials, in a 2 liter flask fitted with a thermometer, stirrer and water trap, for an hour to a maximum temperature of 138° C.

After neutralization of the cooled ester solution with 5% sodium bicarbonate and water, the toluene was removed under water jet vacuum to a pot temperature of 135° c. A high vacuum distillation of the crude ester gave the following results:

| Fr. No. 1 | 130–135° C./3 min. | 89g |
| Fr. No. 2 | 135–152° C./3 min. | 419g |

Analyses of Fractions:

| Analyses of Fractions: | |
|---|---|
| 1st fraction | Acid value = 0.56 |
| | Saponificaton value = 109 |
| | % Chloride = 6.9% |
| | % Ester = 53% |
| | % Alcohol = 47% |
| 2nd fraction | Acid value = 0.25 |
| | Saponification value = 205 |
| | % Chloride = 13% |
| | % Ester = 100% |

Total ester content = 461g
Yield = 84.6% theory

EXAMPLE 11

DECYL MONOCHLORO ACETATE

| Charge: | 316g Decyl alcohol |
|---|---|
| | 208g Monochloro acetic acid |
| | 1g Para toluene sulfonic acid |
| | 250 ml Toluene |
| | 36g water to be removed |

The above materials were refluxed in a 2 liter flask equipped with a thermometer, stirrer and water trap which was fitted with a reflux condenser. The required 36g of water was collected after refluxing, at a maximum temperature of 137° C., for 1½ hrs.

Upon cooling the crude ester solution was washed neutral with 5% sodium bicarbonate followed with water.

Toluene was removed under water jet vacuum to a pot temperature of 135° C.; crude ester was distilled under high vacuum.

| Fr. No. 1 | 113–127° C./3 min. | 123g |
| Fr. No. 2 | 128–130° C./3 min. | 325g |

Analyses of Fractions:

| Analyses of Fractions: | |
|---|---|
| 1st fraction | Acid value = 0.3 |
| | Saponificaton value = 189 |
| | % Chloride = 11.8% |
| | % Ester = 79% |
| | % Decanol = 21% |
| 2nd fraction | Acid value = 0.15 |
| | Saponificaton value = 239 |
| | % Chloride = 15% |
| | % Ester = 100% |

Total ester content = 422.2g
Yield = 90% of theory

EXAMPLE 12

TETRADECYL 3-CHLORO PROPIONATE

| Charge: | 100g 3-chloro propionic acid |
|---|---|
| | 197g Tetradecyl (myristyl) alcohol |
| | 100g Toluene |
| | 17.9g water to be removed |

After refluxing the above material, in a 1 liter flask fitted with a stirrer, thermometer and water trap, for four hours (maximum temp. 148° C.) the required amount of water was removed. The resulting ester solution was neutralized with 5% sodium bicarbonate solution, then washed free of alkali with water. Toluene was removed under water jet vacuum to a pot temperature of 125° C. The crude ester was distilled under high vacuum.

| Fr. No. 1 | 165-195° C./1 min. | 42g |
|---|---|---|
| Fr. No. 2 | 195° C./1 min. | 205g |

| Analyses of Fractions: | |
|---|---|
| 1st fraction | Acid value = 1.2 |
| | Saponificaton value = 22.1 |
| | % Chloride = 1.4% |
| | % Ester = 12% |
| | % Alcohol = 88% |
| 2nd fraction | Acid value = 0.3 |
| | Saponificaton value = 162 |
| | % Chloride = 10.3 |
| | % Ester = 88% |
| | % Alcohol = 12% |
| Wt. of ester = 185.4g | |
| Yield = 89% of theory | |

The material of this invention can be formulated in a variety of manners, e.g. oil in water lotions, or aqueous solutions as a final rinse, as will be readily apparent to the skilled in the art. Typically, the active component is utilized in a concentration of 0.05 wt. % - 5 wt. %; preferably 0.1 - 3 wt. %. Good results have been obtained within these ranges.

The advantages of this invention will be apparent to the skilled in the art. Novel, non-irritating emollients of superior properties are provided from readily available sources.

It will be understood that this invention is not limited to the specific examples which have been offered as particular embodiments, and that modifications can be made without departing from the spirit thereof.

What is claimed is:

1. As a novel emollient, hair conditioning, composition of matter a fatty halo alkanoate quaternary of dialkyl amino propyl amides, corresponding to the formula

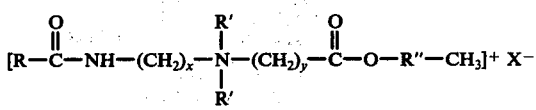

wherein the RCO moiety is selected from the group consisting of gluconic acid, and $C_7$-$C_{21}$ fatty acids; R' is an alkyl group having from 1 to 2 carbon atoms; x is an integer of from 2 to 3; y is an integer of from 1 to 3; R'' is selected from the group consisting of $(CH_2)_{(7-21)}$ and sorbate; and X is halogen.

2. The composition of claim 1 in which R' is $CH_3$; x is 3; y is 1; R'' is $(CH_2)_{13}$; and X is Cl.

3. The composition of claim 2 in which the RCO moiety is gluconic acid.

4. The composition of claim 2 in which the RCO moiety is safflower fatty acids.

5. The composition of claim 2 in which the RCO moiety is hydrogenated tallow triglycerides.

6. The composition of claim 2 in which the RCO moiety is mink oil fatty acids.

* * * * *